United States Patent
Oftring et al.

(10) Patent No.: US 7,652,165 B2
(45) Date of Patent: Jan. 26, 2010

(54) NEUTRALIZATION OF ISOPHORONE NITRILE SYNTHESIS PRODUCTS

(75) Inventors: Alfred Oftring, Bad Duerkheim (DE); Gerold Braun, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 602 days.

(21) Appl. No.: 10/539,134

(22) PCT Filed: Dec. 16, 2003

(86) PCT No.: PCT/EP03/14292

§ 371 (c)(1), (2), (4) Date: Jun. 16, 2005

(87) PCT Pub. No.: WO2004/056753

PCT Pub. Date: Jul. 8, 2004

(65) Prior Publication Data

US 2006/0058544 A1    Mar. 16, 2006

(30) Foreign Application Priority Data

Dec. 19, 2002   (DE) ................................ 102 59 708

(51) Int. Cl.
*C07C 253/12* (2006.01)
(52) U.S. Cl. .................................................... 558/341

(58) Field of Classification Search .................. 558/341
See application file for complete search history.

(56) References Cited

U.S. PATENT DOCUMENTS

| 5,011,968 A | 4/1991 | Thunberg et al. |
| 5,183,915 A | 2/1993 | Forguy et al. |
| 5,235,089 A | 8/1993 | Woodbury et al. |

FOREIGN PATENT DOCUMENTS

| DE | 1 085 871 | 7/1960 |
| DE | 1 240 854 | 5/1967 |
| DE | 39 42 371 | 6/1991 |
| EP | 0 671 384 | 9/1995 |
| EP | 0 985 659 | 3/2000 |

*Primary Examiner*—James O Wilson
*Assistant Examiner*—Ebenezer Sackey
(74) *Attorney, Agent, or Firm*—Oblon, Spivak, McClelland, Maier & Neustadt, L.L.P.

(57) ABSTRACT

The present invention relates to a process for preparing 3-cyano-3,5,5-trimethylcyclohexanone (isophoronenitrile) by reacting isophorone with hydrogen cyanide in the presence of a base as a catalyst to obtain a crude isophoronenitrile product, and subsequently distilling the crude isophoronenitrile product, with the addition before distillation of at least one specific sulfonic acid or specific carboxylic acid. In addition, the present invention relates to the use of a specific sulfonic acid or of a specific carboxylic acid as a neutralizing agent before distillation of a crude isophoronenitrile product which has been obtained by reacting isophorone with hydrogen cyanide in the presence of a base as a catalyst, in order to avoid precipitates in the neutralization of the base used as a catalyst with an acid.

16 Claims, No Drawings

NEUTRALIZATION OF ISOPHORONE NITRILE SYNTHESIS PRODUCTS

The present invention relates to a process for preparing 3-cyano-3,5,5-trimethylcyclohexanone (isophoronenitrile) by reacting isophorone with hydrogen cyanide in the presence of a base as a catalyst, the base used as a catalyst being neutralized before a distillation following the reaction, and also to the use of specific sulfonic acids or carboxylic acids for neutralizing a base used as a catalyst in a process for preparing isophoronenitrile.

3-Cyano-3,5,5-trimethylcyclohexanone (isophoronenitrile) is an industrially significant intermediate. Aminating hydrogenation converts isophoronenitrile to 1-amino-3-aminomethyl-3,5,5-trimethylcyclohexane (isophoronediamine) which is used for preparing epoxy resins, as a crosslinking agent and also as a special monomer in polyurethane production.

In general, isophoronenitrile is prepared under base catalysis by addition of hydrogen cyanide to isophorone at elevated temperature. Before a subsequent distillative workup of the crude isophoronenitrile product, it is advantageous to neutralize the base used as a catalyst, in order to avoid decomposition or dissociation reactions of the isophoronenitrile and an associated loss of yield.

For instance, DE-A 39 42 371 relates to a process for preparing isophoronenitrile by reacting isophorone with hydrogen cyanide in the presence of lithium hydroxide as a catalyst, and the lithium hydroxide used is neutralized by phosphoric acid or p-toluenesulfonic acid. When these compounds are used to neutralize the base used as a catalyst, crystalline precipitates are formed which lead to considerable problems caused by deposits in the neutralization reactor and in the downstream distillation column.

DE-A 1 085 871 likewise relates to a process for preparing alicyclic cyano ketones, in particular isophoronenitrile, by reacting hydrogen cyanide with isophorone in the presence of a strongly alkaline catalyst which forms cyanide ions. According to the examples, the neutralizing agent used is phosphoric acid which, as already mentioned above, leads to the occurrence of crystalline precipitates.

U.S. Pat. No. 5,183,915 likewise relates to a process for preparing isophoronenitrile by reacting isophorone with hydrogen cyanide at elevated temperatures and pressures in the presence of a quaternary ammonium cyanide or quaternary phosphonium cyanide as a catalyst.

DE-A 1 240 854 relates in turn to a process for preparing isophoronenitrile by reacting isophorone with hydrogen cyanide in the presence of strongly alkaline catalysts which form cyanide ions. According to the examples, nitric acid is added as a neutralizing agent after the reaction. The addition of nitric acid too results in the formation of crystalline precipitates which lead to considerable problems caused by deposits in the neutralization reactor or in the downstream distillation column.

U.S. Pat. No. 5,235,089 relates to a process for preparing isophoronenitrile by reacting isophorone with hydrogen cyanide in the presence of lithium hydroxide or lithium cyanide as a catalyst. In order to acidify the reaction mixture, a polyacidic acid can be added. This is followed by a filtration, in order to remove the precipitated lithium salt of the acid used from the reaction mixture. Suitable polyacidic acids are maleic acid, oxalic acid, sulfuric acid and phosphoric acid. According to the description in U.S. Pat. No. 5,235,089, the use of maleic acid results in crystalline precipitates of the corresponding dilithium salt, and the use of phosphoric acid results in fine precipitates in the form of $LiH_2PO_4$ which are difficult to filter.

The precipitates formed in the neutralization according to the prior art can lead to considerable problems caused by deposits in the neutralization reactor and in the downstream distillation column. For example, as a consequence of these precipitates, frequent cleaning operations are necessary, which entails economically disadvantageous plant downtimes. In addition, the deposits cause reduced distillation yields and increased amounts of residue, which have to be disposed of in a costly and inconvenient manner.

It is an object of the present invention, therefore, to provide a process for preparing isophoronenitrile by reacting isophorone with hydrogen cyanide in the presence of a base as a catalyst, wherein the base is neutralized before a distillation of the crude isophoronenitrile product in such a way that no sedimenting precipitates occur. This allows the process costs in the preparation of pure isophoronenitrile to be considerably reduced.

We have found that this object is achieved by a process for preparing 3-cyano-3,5,5-trimethylcyclohexanone (isophoronenitrile) by reacting isophorone with hydrogen cyanide in the presence of a base as a catalyst to obtain a crude isophoronenitrile product, and subsequently distilling the crude isophoronenitrile product.

A feature of the process according to the invention is the addition before the distillation of at least one sulfonic acid or carboxylic acid selected from the group consisting of

$$R-SO_3H$$

where R is a linear or branched $C_1$- to $C_{24}$-alkyl radical which may optionally be substituted by $-CO_2R'$ where R' is hydrogen or an alkyl radical, or by one or more phosphonic acid groups; a phenyl radical substituted by linear or branched $C_2$- to $C_{24}$-alkyl radicals, nitro, sulfo or hydroxyl groups; or a substituted or unsubstituted fused aromatic radical;

aliphatic polysulfonic acids; condensates of naphthalene- or phenolsulfonic acids; aliphatic polycarboxylic acids; and

$$R''-CO_2H$$

where R'' is a linear or branched $C_2$- to $C_{24}$-alkyl radical which may optionally be substituted by one or more phosphonic acid groups; a phenyl radical which is unsubstituted or substituted by linear or branched $C_1$- to $C_{24}$-alkyl groups, nitro, sulfo or hydroxyl groups; or an unsubstituted or substituted fused aromatic radical.

Suitable sulfonic acids $R-SO_3H$ are therefore aliphatic monosulfonic acids where R is preferably a linear or branched $C_1$- to $C_{24}$-alkyl radical. Particular preference is given to using methanesulfonic acid, ethanesulfonic acid and propanesulfonic acid, very particular preference is given to using methanesulfonic acid. Also suitable are aliphatic polysulfonic acids, preferably having from 2 to 100, more preferably from 10 to 50, sulfonic acid groups, for example homo- or copolymers of vinyl- or allylsulfonic acid, and also sulfonated polyunsaturated fats. Suitable sulfonic acids $R-SO_3H$ where R is a phenyl radical substituted by linear or branched $C_2$- to $C_{24}$-alkyl radicals, preferably by $C_4$- to $C_{16}$-alkyl radicals are in particular linear alkylbenzenesulfonic acids which are preferably used in the form of mixtures. Also suitable are benzenesulfonic acids which are substituted by nitro, sulfo or hydroxyl groups. Suitable substituted or unsubstituted fused aromatic sulfonic acids are in particular fused aromatic sulfonic acids based on naphthalene. Particular preference is given to naphthalenemono-, -di- and -trisulfonic acids. Preference is also given to using alkyl-substituted naphthalenesulfonic acids, e.g. diisobutyl-naphthalenesulfonic acid. Suitable sulfocarboxylic acids are in particular sulfosuccinic acid.

The alkyl-substituted benzenesulfonic acids preferably have an alkyl radical having ≧4 carbon atoms.

Very particular preference is given to using methanesulfonic acid, naphthalene- or alkyl-substituted naphthalenesulfonic acids and alkyl-substituted benzenesulfonic acids having an alkyl radical having ≧4 carbon atoms, preferably from 6 to 14 carbon atoms. Very particular preference is given to $C_{12}$-alkylbenzenesulfonic acid.

Suitable aliphatic polycarboxylic acids generally have ≧3 carbonyl groups, preferably from 3 to 100 carbonyl groups. Particularly preferred carboxylic acids R"—CO$_2$H are aliphatic carboxylic acids where R" is a $C_2$- to $C_{10}$-alkyl radical which may be branched or unbranched. Very particularly preferred aliphatic carboxylic acids are propionic acid, pivalic acid, 2-ethylhexanoic acid and isononanoic acid.

The sulfonic acids or carboxylic acids mentioned serve as neutralizing agents for neutralizing the base used as a catalyst, in order to avoid decomposition and/or dissociation reactions of the isophoronenitrile. In contrast to the prior art, when the sulfonic acids or carboxylic acids listed in accordance with the present invention are used as neutralizing agents, no precipitate is formed. This allows the workup of the crude isophoronenitrile product to be carried out without additional operations such as filtration.

The sulfonic acids and carboxylic acids used in accordance with the invention are generally used in the form of their highly concentrated aqueous solution, for example from ≧30% by weight to 80% by weight of the acids used in accordance with the invention in water, or pure, for example where methanesulfonic acid or dodecylbenzenesulfonic acid are used.

The sulfonic acids or carboxylic acids mentioned can be used alone or in a mixture with further acids for neutralization. Preference is given to using each of the sulfonic acids mentioned alone. It is also possible to use one or more of the sulfonic acids mentioned in a mixture with inorganic mineral acids, for example phosphoric acid or sulfuric acid, but only in a proportion of inorganic mineral acids which causes no salt precipitation. The precise proportion depends on the base used as a catalyst and also on the sulfonic acid or carboxylic acid used.

In a preferred embodiment, a mixture of from 60 to 95% by weight, preferably from 70 to 80% by weight, of an alkyl-substituted naphthalenesulfonic acid, from 3 to 39% by weight, preferably from 5 to 15% by weight, of sulfuric acid, and from 0 to 20% by weight, preferably from 0.5 to 15% by weight, of water, is used.

Suitable catalysts are preferably bases selected from the group consisting of alkali metal and alkaline earth metal carbonates, alkali metal and alkaline earth metal alkoxides, oxides, hydroxides and cyanides, tertiary amines and quaternary phosphonium and ammonium bases. Suitable catalysts are, for example, sodium ethoxide, potassium butoxide, lithium ethoxide, magnesium ethoxide, sodium methoxide, potassium methoxide, lithium methoxide, magnesium methoxide, sodium oxide, potassium hydroxide, calcium oxide, barium hydroxide, strontium hydroxide, sodium cyanide, potassium cyanide, lithium cyanide, barium cyanide, magnesium cyanide, calcium cyanide, sodium carbonate, potassium carbonate, trimethylamine, triethylamine, triethanolamine, octyldimethylamine, N-methylmorpholine, benzyltrimethylammonium hydroxide, dibenzyldimethylammonium hydroxide, dodecyltriethylammonium hydroxide and quaternary phosphonium salts, preferably in the form of hydroxides, cyanides, hydrogencarbonates and alkylcarbonates. Particularly preferred catalysts are alkali metal and alkaline earth metal cyanides, alkali metal and alkaline earth metal hydroxides, alkali metal and alkaline earth metal oxides and alkali metal and alkaline earth metal alkoxides. Very particular preference is given to sodium hydroxide, potassium hydroxide, magnesium hydroxide, calcium hydroxide, sodium oxide, potassium oxide, magnesium oxide, calcium oxide, sodium cyanide, potassium cyanide, magnesium cyanide, calcium cyanide and sodium methoxide.

The base used as a catalyst is generally used in an amount of from 0.01 to 20% by weight, based on the isophorone used, preferably from 0.05 to 5% by weight, more preferably from 0.1 to 1% by weight.

The molar ratio of isophorone to hydrogen cyanide in the process according to the invention is generally from 0.6:1 to 7:1, preferably from 1:1 to 3:1, more preferably from 1.3:1 to 2.5:1. Where an excess of isophorone is used in the process according to the invention, this may simultaneously serve as a solvent.

In general, the process according to the invention is carried out in the absence of solvents, unless an excess of isophorone serves as the solvent. However, it is also possible to carry out the process according to the invention in a solvent. Suitable solvents are dimethylformamide, N,N-dimethylacetamide, N-methyl-2-pyrrolidone, glycols or glycol ethers.

The process according to the invention is generally carried out at temperatures of from 80 to 220° C., preferably from 120 to 200° C., more preferably from 150 to 200° C. The pressure in the process according to the invention is generally from 1 to 5 bar, preferably from 1 to 3 bar.

The product is obtained in very high purity by the process according to the invention.

The sulfonic acid or carboxylic acid used to neutralize the base used as a catalyst is used in an amount of generally from 0.5 to 2, preferably from 0.7 to 1.3, more preferably from 0.9 to 1.1, most preferably 1, acid equivalent(s), based on 1 base equivalent of the base used as a catalyst.

The sulfonic acid or carboxylic acid added in accordance with the invention is added before the distillation of the isophoronenitrile reaction product obtained in the reaction according to the invention. Preference is given to adding after the end of the reaction of the isophorone with hydrogen cyanide.

After the addition of the sulfonic acid or carboxylic acid used in accordance with the invention, the crude isophoronenitrile product is distilled. In general, a fractional distillation is carried out under reduced pressure.

In a preferred embodiment of the present invention, the process according to the invention comprises the following steps:

a) isophoronenitrile synthesis by reaction of isophorone with hydrogen cyanide in the presence of a base as a catalyst to obtain a crude isophoronenitrile product, b) neutralization of the reaction mixture obtained in step a) with a sulfonic acid or carboxylic acid selected from the group consisting of

where R is a linear or branched $C_1$- to $C_{24}$-alkyl radical which may optionally be substituted by —CO$_2$R' where R' is hydrogen or an alkyl radical, or by one or more phosphonic acid groups, a phenyl radical substituted by linear or branched $C_2$- to $C_{24}$-alkyl radicals, nitro, sulfo or hydroxyl groups; or a substituted or unsubstituted fused aromatic radical; aliphatic polysulfonic acids;

condensates of naphthalene- or phenolsulfonic acids, aliphatic polycarboxylic acids; and

where R" is a linear or branched $C_2$- to $C_{24}$-alkyl radical which may optionally be substituted by one or more phosphonic acid groups; a phenyl radical which is substituted by linear or branched $C_1$- to $C_{24}$-alkyl groups, nitro, sulfo or hydroxyl groups; or an unsubstituted or substituted fused aromatic radical, c) distillation of the reaction mixture obtained in step b).

Preferred embodiments of steps a), b) and c) and the components used therein have already been mentioned above.

It is possible to carry out the isophoronenitrile synthesis, subsequent neutralization and distillative workup each in itself continuously, semicontinuously or batchwise. Preference is given to carrying out the isophoronenitrile synthesis (reaction) itself continuously or semicontinuously, the neutralization (addition of the sulfonic acid or carboxylic acid) continuously or semicontinuously, and the subsequent distillation (distillative workup) continuously or semicontinuously. Particular preference is given to carrying out the isophoronenitrile synthesis, the neutralization and the subsequent distillation continuously.

The individual process steps can be carried out in separate reactors. Suitable reactors are known to those skilled in the art. In one embodiment of the process according to the invention, both the isophoronenitrile synthesis and the subsequent neutralization are carried out in the batchwise method. In this embodiment, the isophoronenitrile synthesis and subsequent neutralization are preferably carried out in the same reactor. In the further possible embodiments, preference is given to carrying out the individual process steps in separate reactors. The subsequent distillation is generally effected using a rectification column. In principle, all suitable reactor types can be used.

The present application further relates to the use of a sulfonic acid or carboxylic acid selected from the group consisting of $$R\!-\!SO_3H$$

where R is a linear or branched $C_1$- to $C_{24}$-alkyl radical which may optionally be substituted by —$CO_2R'$ where R' is hydrogen or an alkyl radical, or by one or more phosphonic acid groups, a phenyl radical substituted by linear or branched $C_2$- to $C_{24}$-alkyl radicals, nitro, sulfo or hydroxyl groups, or a substituted or unsubstituted fused aromatic radical;

aliphatic polysulfonic acids; condensates of naphthalene- or phenolsulfonic acids, aliphatic polycarboxylic acids; and

where R" is a linear or branched $C_2$- to $C_{24}$-alkyl radical which may optionally be substituted by one or more phosphonic acid groups, a phenyl radical which is unsubstituted or substituted by linear or branched $C_1$- to $C_{24}$-alkyl groups, nitro, sulfo or hydroxyl groups; or an unsubstituted or substituted fused aromatic radical, as a neutralizing agent in the distillation of a crude isophoronenitrile product which has been obtained by reacting isophorone with hydrogen cyanide in the presence of a base as a catalyst, in order to avoid precipitates in neutralization.

Preferred sulfonic acids and carboxylic acids have been mentioned above.

In this context, neutralization and neutralizing agents are the neutralization of the base which is used as a catalyst and can cause, in the course of the purification of the crude isophoronenitrile product by distillation, decomposition and/or dissociation reactions of the isophoronenitrile obtained as the product of value, and the compound(s) used for neutralization respectively.

The invention is illustrated by the examples which follow.

EXAMPLES

Example 1

Comparative Example 500 g of a crude isophoronenitrile synthesis solution comprising 54.8% by weight of isophoronenitrile (=274 g), 41.1% of isophorone (=206 g) and 0.3% of sodium cyanide (=1.5 g=0.03 mol) were initially charged in a batch distillation apparatus. The base was neutralized at 50° C. with 3.9 g of 75% aqueous phosphoric acid.

A coarsely crystalline solid precipitated out immediately. The mixture was fractionally distilled at 50 mbar for approx. 2 hours up to a bottom temperature of approx. 200° C.

Yield:

| | |
|---|---|
| isophorone: 195 g | isophoronenitrile: 245 g |
| distillation residue: 48 g (crystalline) | |

Example 2

Comparative Example

Crude isophoronenitrile solution as in Example 1. Instead of the phosphoric acid, 4.8 g of toluenesulfonic acid were used for neutralization.

A crystalline solid precipitated out, although it was more fine than in Example 1. The distillation conditions were similar to Example 1.

Yield:

| | |
|---|---|
| isophorone: 198 g | isophoronenitrile: 253 g |
| residue: 44 g (solid) | |

Example 3

Inventive

Crude isophoronenitrile solution as in Example 1. For neutralization, 4.1 g of 70% aqueous methanesulfonic acid were used.

There was no crystalline precipitate. The distillation conditions were similar to Example 1.

Yield:

| | |
|---|---|
| isophorone: 202 g | isophoronenitrile: 259 g |
| residue: 19 g (the oil solidified in a glasslike manner only below 50° C.) | |

Example 4

Inventive

Crude isophoronenitrile solution as in Example 1. For neutralization, 9.1 g of Nekal SBC® of the following composition was used: 75% by weight of diisobutylnaphthalenesulfonic acid, 10% by weight of sulfuric acid and 15% by weight of water.

There was neither a crystalline precipitate nor cloudiness. The distillation conditions were similar to Example 1.

Yield:

| | |
|---|---|
| isophorone: 201 g | isophoronenitrile: 265 g |
| residue: 15 g (remains an oil even at room temperature) | |

Example 5

Inventive

Crude isophoronenitrile solution as in Example 1. For neutralization, 9.7 g of dodecylbenzenesulfonic acid (LAS (linear alkylbenzenesulfonic acid, Lutensit® ALBS)—having $C_{12}$-alkyl on average) were used.

There was no precipitate or cloudiness at all. The distillation conditions were similar to Example 1.

Yield:

| | |
|---|---|
| isophorone: 200 g | isophoronenitrile: 263 g |
| residue: 18 g (oil) | |

Example 6

Comparative Example 500 g of crude isophoronenitrile of the following composition were used: 41.7% of isophorone (=210 g), 55.3% of isophoronenitrile (=277 g), 1.7 g of calcium oxide (=0.03 mol). For neutralization, 3.9 g of 75% aqueous phosphoric acid were used. A coarsely crystalline solid precipitated out immediately. The distillation conditions were similar to Example 1.

Yield:

| | |
|---|---|
| isophorone: 198 g | isophoronenitrile: 248 g |
| residue: 38 g (solid) | |

Example 7

Inventive

The procedure was similar to Example 6. For neutralization, 4.1 g of 70% aqueous methanesulfonic acid were used.

No solid precipitated out. The distillation conditions were similar to Example 1.

Yield:

| | |
|---|---|
| isophorone: 203 g | isophoronenitrile: 264 g |
| residue: 18 g (solidified in a glasslike manner only below 50° C.) | |

Example 8

Inventive

Crude isophoronenitrile solution as in Example 1. For neutralization, 4.3 g of 2-ethylhexanoic acid were used.

There was only slight cloudiness. The distillation conditions were similar to Example 1.

Yield:

| | |
|---|---|
| isophorone: 201 g | isophoronenitrile: 259 g |
| residue: 25 g (viscous oil) | |

We claim:

1. A process for preparing 3-cyano-3,5,5-trimethylcyclohexanone (isophoronenitrile), comprising
   reacting isophorone with hydrogen cyanide in the presence of a base as a catalyst to form a crude isophoronenitrile product, and
   subsequently distilling the crude isophoronenitrile product to prepare the isophoronenitrile,
   wherein the base is selected from the group consisting of an alkali metal cyanide, an alkaline earth metal cyanide, an alkali metal hydroxide, an alkaline earth metal hydroxide, an alkali metal oxide, an alkaline earth metal oxide, an alkali metal alcoholate and an alkaline earth metal alcoholate,
   wherein, before the distilling, at least one sulfonic acid is added,
   wherein the at least one sulfonic acid is selected from the group consisting of methanesulfonic acid, a naphthalenesulfonic acid, an alkyl-substituted naphthalenesulfonic acid, an alkyl-substituted benzenesulfonic acid having an alkyl radical having greater than or equal to 4 carbon atoms, and combinations thereof, and
   wherein the addition of the at least one sulfonic acid neutralizes the base in such a way that no sedimenting precipitates occur.

2. The process of claim 1, wherein the at least one sulfonic acid is added in an amount of 1 acid equivalent, based on 1 base equivalent of the base used as the catalyst.

3. The process of claim 1, wherein the base used as the catalyst is used in an amount of from 0.01 to 20% by weight, based on the isophorone used.

4. The process of claim 1, wherein the reacting is carried out at temperatures of from 80 to 220° C.

5. The process of claim 1, wherein the reacting is carried out at a pressure of from 1 to 5 bar.

6. The process of claim 1, wherein the distilling is carried out in a rectification column.

7. The process of claim 1, wherein the reacting, the addition of the at least one sulfonic acid, and the subsequent distilling are carried out continuously.

8. A process for preparing 3-cyano-3,5,5-trimethylcyclohexane (isophoronenitrile), comprising
   a) reacting isophorone with hydrogen cyanide in the presence of a base as a catalyst to obtain a reaction mixture comprising a crude isophoronenitrile product,
   b) neutralizing the reaction mixture from a) with at least one sulfonic acid to obtain a neutralized reaction mixture, and
   c) distilling the neutralized reaction mixture obtained in b),
   wherein the base is selected from the group consisting of an alkali metal cyanide, an alkaline earth metal cyanide, an alkali metal hydroxide, an alkaline earth metal hydroxide, an alkali metal oxide, an alkaline earth metal oxide, an alkali metal alcoholate and an alkaline earth metal alcoholate;
   wherein the at least one sulfonic acid is selected from the group consisting of methanesulfonic acid, a naphthalenesulfonic acid, an alkyl-substituted naphthalenesulfonic acid, an alkyl-substituted benzenesulfonic acid having an alkyl radical having greater than or equal to 4 carbon atoms, and combinations thereof; and
   wherein the addition of the at least one sulfonic acid neutralizes the base in such a way that no sedimenting precipitates occur.

9. A method for avoiding precipitates in the neutralization of a base used as a catalyst in the reaction of isophorone with hydrogen cyanide in the presence of said base, the method comprising
   adding at least one sulfonic as a neutralizing agent before a distillation of a crude isophoronenitril product which has been obtained by said reaction,
   wherein the base is selected from the group consisting of an alkali metal cyanide, an alkaline earth metal cyanide, an alkali metal hydroxide, an alkaline earth metal hydroxide, an alkali metal oxide, an alkaline earth metal oxide, an alkali metal alcoholate and an alkaline earth metal alcoholate; and
   wherein the at least one sulfonic acid is selected from the group consisting of methanesulfonic acid, a naphthalenesulfonic acid, an alkyl-substituted naphthalenesulfonic acid, an alkyl-substituted benzenesulfonic acid having an alkyl radical having greater than or equal to 4 carbon atoms, and combinations thereof; and
   wherein the addition of the at least one sulfonic acid neutralizes the base in such a way that no sedimenting precipitates occur.

10. The process of claim 1, wherein the at least one sulfonic acid is diisobutylnaphthalenesulfonic acid or dodecylbenzenesulfonic acid.

11. The method of claim 8, wherein the at least one sulfonic acid is diisobutylnaphthalenesulfonic acid or dodecylbenzenesulfonic acid.

12. The process of claim 1, wherein the base is sodium cyanide and the at least one sulfonic acid selected from the group consisting of, methanesulfonic acid, diisobutylnaphthalenesulfonic acid, dodecylbenzenesulfonic acid and combinations thereof.

13. The method of claim 1, wherein the at least one sulfonic acid is selected from the group consisting of methanesulfonic acid, diisobutylnaphthalenesulfonic acid, dodecylbenzenesulfonic acid, and combinations thereof; and the base is sodium cyanide.

14. The process of claim 1, wherein the reacting is carried out at temperatures of from 120 to 200° C.

15. The process of claim 1, wherein the reacting is carried out at temperatures of from 150 to 200° C.

16. The process of claim 1, wherein the reaction is carried out at a pressure of from 1 to 3 bar.

* * * * *